United States Patent
Gueritee et al.

(10) Patent No.: US 12,220,007 B2
(45) Date of Patent: Feb. 11, 2025

(54) ELECTRICAL ACTIVE ASSEMBLY AND A CLOTHING ASSEMBLY COMPRISING THE SAME

(71) Applicant: CLIM8, Tassin-la-Demi-Lune (FR)

(72) Inventors: Julien Gueritee, Eveux (FR); Florian Miguet, Venissieux (FR); Pierre Mouette, HK (CN)

(73) Assignee: CLIM8, Tassin-la-Demi-Lune (FR)

( * ) Notice: Subject to any disclaimer, the term of this patent is extended or adjusted under 35 U.S.C. 154(b) by 721 days.

(21) Appl. No.: 17/417,564

(22) PCT Filed: Dec. 24, 2018

(86) PCT No.: PCT/IB2018/001609
§ 371 (c)(1),
(2) Date: Jun. 23, 2021

(87) PCT Pub. No.: WO2020/136386
PCT Pub. Date: Jul. 2, 2020

(65) Prior Publication Data
US 2022/0053844 A1  Feb. 24, 2022

(51) Int. Cl.
*A41D 13/005* (2006.01)
*A41D 1/00* (2018.01)
(Continued)

(52) U.S. Cl.
CPC ......... *A41D 13/0051* (2013.01); *A41D 1/002* (2013.01); *A41D 13/0053* (2013.01); *H05B 1/0272* (2013.01); *H05B 3/342* (2013.01)

(58) Field of Classification Search
CPC ...... H05B 1/0272; H05B 3/342; H05B 3/345; H05B 3/347; A41D 13/005; A41D 13/0053; A41D 13/0051; A41D 1/002
See application file for complete search history.

(56) References Cited

U.S. PATENT DOCUMENTS

| 2007/0063849 | A1  | 3/2007 | Rosella et al. |
| 2015/0230524 | A1* | 8/2015 | Stevens ............ H05B 1/02 219/494 |
| 2016/0062333 | A1* | 3/2016 | Jayaraman ......... G08C 17/02 700/11 |

FOREIGN PATENT DOCUMENTS

WO  2016033512 A1  3/2016

OTHER PUBLICATIONS

International search report and Written Opinion issued for PCT/IB2018/001609.

* cited by examiner

*Primary Examiner* — Brian W Jennison
(74) *Attorney, Agent, or Firm* — AEON Law, PLLC; Adam L. K. Philipp; Charlotte E. Holoubek

(57) ABSTRACT

The invention relates to an electrical active assembly for generating a physical effect such as heat, cold or humidity, and a textile assembly, such as a clothing assembly, including said electrical active assembly, with an application to a system for regulating the temperature or humidity of a user's body.

Figure 1:
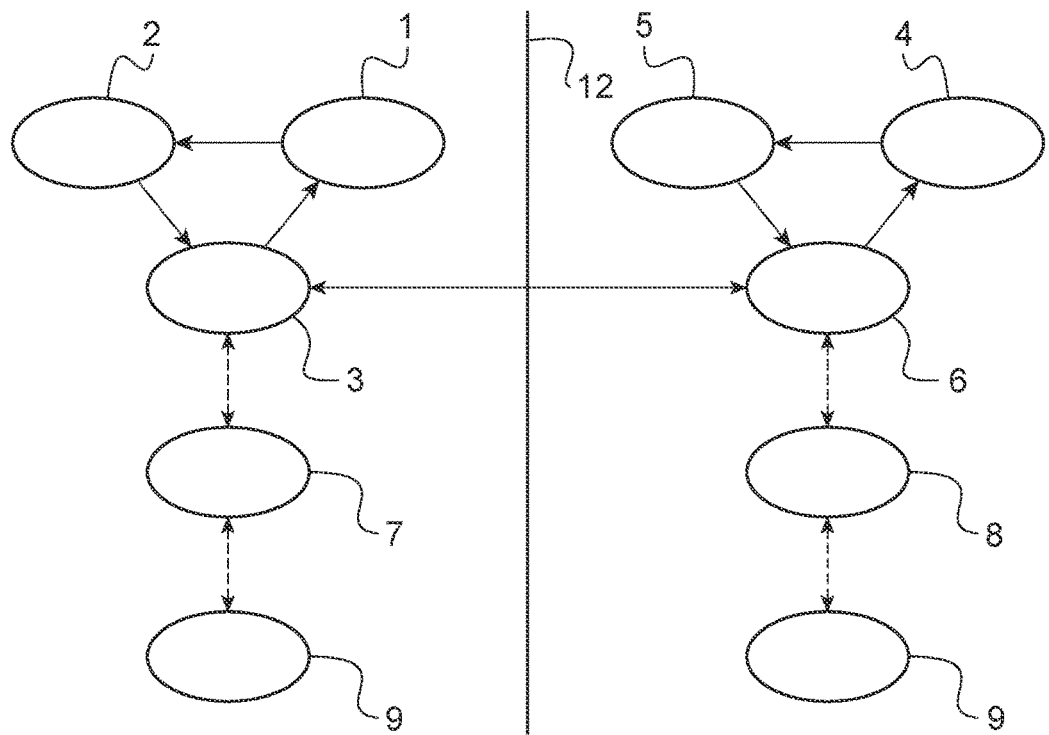

The electrical assembly comprises a first textile support, a first active element 1 for generating the physical effect, connected to a power source, and located on or in the first textile support, a first sensor 2 for sensing data relative to a physical information, such as temperature or humidity, connected to a power source, and located on or in the first textile support, and a first controlling unit 3 connected to the first active element and sensor, and located on or in the first textile support, such as to allow the activation/deactivation by the first controlling unit of the first active element depending on data sensed by the first sensor.

The electrical assembly also comprises a second textile support distinct from the first textile support, a second active (Continued)

element 4 for generating said physical effect, connected to a power source, and located on or in the second textile support, a second sensor 5 for sensing data relative to the physical information, connected to a power source, and located on or in the second textile support, and a second controlling unit 6 connected to the second active element and sensor, and located on or in said second textile support, such as to allow the activation/deactivation by the second controlling unit of the second active element depending on data sensed by the second sensor.

The first controlling unit is connected to the second active element and sensor, such as to allow the activation/deactivation by the first controlling unit of the second active element depending on data sensed by the second sensor and/or by the first sensor, and/or the second controlling unit is connected to the first active element and sensor, such as to allow the activation/deactivation by the second controlling unit of the first active element depending on data sensed by the first sensor and/or by the second sensor.

15 Claims, 1 Drawing Sheet

(51) Int. Cl.
 *H05B 1/02* (2006.01)
 *H05B 3/34* (2006.01)

ELECTRICAL ACTIVE ASSEMBLY AND A CLOTHING ASSEMBLY COMPRISING THE SAME

RELATED APPLICATIONS

This application is a U.S. national phase entry of and claims priority to PCT International Phase Application No. PCT/IB2018/001609, filed Dec. 24, 2018. The entire contents of the above-referenced applications and of all priority documents referenced in the Application Data Sheet filed herewith are hereby incorporated by reference for all purposes.

FIELD OF THE INVENTION

The present invention relates to an electrical active assembly for generating a physical effect such as heat, cold or humidity, with a particular application to a temperature regulation system for regulating the temperature or humidity of a portion of a body, in particular of a user's body.

The invention also relates to a textile assembly, such as a clothing assembly, including said electrical active assembly.

BACKGROUND OF THE INVENTION

Thermal comfort is driven by the temperature inside a person's body and the temperature at the surface of your body. Deep body temperature of a person is generally 37° C. and the mean skin temperature of a person is generally 33° C. People become uncomfortable in a thermal sense when the environment changes for example, increased wind or extra sunny day, or when a person moves to a cooler place. In common situations, discomfort in a thermal sense is felt by a user when the user's skin temperature changes, rather than a change in core body temperature.

Conventional chemical or electric heating systems used in clothing can easily deliver heat at relatively high levels. Most currently available devices consist of a wearable garment with heating pads that can be manually adjusted by the user. In at least some devices the heating pads produce an equal heat output and all the heating pads are activated to provide heat. Existing products are often bulky, heavy, require manual operation and are limited in their range of operation.

When the user wants to wear two pieces of garment, whether for superposing the two pieces, such as a shirt and a jacket, on the same part of his/her body or for wearing the two pieces, such as a glove and a shirt, on different parts of his/her body, with the two pieces each comprising their own electric heating system, the user has to adjust the settings of both separately, and the working of both pieces is independent from each other. This prevents from taking into account what happens around one of the parts of the user's body for the efficiency of the system corresponding to the other part of the user's body. This also prevents from taking into account what happens around one of the pieces of garment for the efficiency of the system corresponding to the other piece of garment.

On top of this, when one of the electric systems in one of the two pieces of garment fails, the user has to have the electric system repaired or buy a new piece of garment.

SUMMARY OF THE INVENTION

The invention aims therefore at solving the problems mentioned, amongst other problems.

To this end, the invention proposes an electrical assembly with two independent textile support embodying components for local physical effect active regulation, allowing cross regulation.

According to a first aspect, the object of the invention is an electrical active assembly for generating at least one physical effect such as heat, cold or relative humidity, comprising
  a first textile support;
  a first active element adapted for generating said physical effect and for being connected to a power source, and located on or in said first textile support;
  a first sensor adapted for sensing data relative to a physical information, such as temperature or humidity, and being connected to a power source, and located on or in said first textile support;
  and a first controlling unit connected to the first active element and the first sensor, and located on or in said first textile support;
such as to allow the activation/deactivation by said first controlling unit of said first active element depending on data sensed by said first sensor.

The electrical assembly further comprises:
  a second textile support distinct from said first textile support;
  a second active element adapted for generating said physical effect and for being connected to a power source, and located on or in said second textile support;
  a second sensor adapted for sensing data relative to a physical information and being connected to a power source, and located on or in said second textile support;
  and a second controlling unit connected to the second active element and the second sensor, and located on or in said second textile support;
such as to allow the activation/deactivation by said second controlling unit of said second active element depending on data sensed by said second sensor.

The first controlling unit is connected to the second active element and the second sensor, such as to allow the activation/deactivation by said first controlling unit of said second active element depending on data sensed by said second sensor and/or by said first sensor, and/or the second controlling unit is connected to the first active element and the first sensor, such as to allow the activation/deactivation by said second controlling unit of said first active element depending on data sensed by said first sensor and/or by said second sensor.

In some embodiments, the electrical active assembly further comprises one or more of the following features, considered alone or according to any technically possible combination:
  the second active element and the second sensor are directly connected to the first controlling unit through respective direct connection points, such as to allow the direct activation/deactivation by said first controlling unit of said second active element through the corresponding connection point, depending on data sensed by said second sensor and received by said first controlling unit through the corresponding connection point, and/or on data sensed by the first sensor and received by said first or second controlling unit;
  the first active element and the first sensor are directly connected to the second controlling unit through respective direct connection points, such as to allow the direct activation/deactivation by said second controlling unit of said first active element through the corresponding connection point, depending on data sensed by said first sensor and received by said second controlling unit through the corresponding connection point, and/or on data sensed by the second sensor and received by said first or second controlling unit;

the second controlling unit is able to connect with the first controlling unit such as to allow the activation/deactivation by the second controlling unit of the first active element through the first controlling unit, depending on data sensed by the first sensor and received by the second controlling unit through the first controlling unit, and/or on data sensed by the second sensor received by said second controlling unit;

the first controlling unit is able to connect with the second controlling unit such as to allow the activation/deactivation by the first controlling unit of the second active element through the second controlling unit, depending on data sensed by the second sensor and received by the first controlling unit through the second controlling unit, and/or on data sensed by the first sensor received by said first controlling unit.

According to a second aspect, the object of the invention is also a textile assembly, such as a clothing assembly to be worn by a human or animal user, comprising an electrical active assembly as presented above.

In some embodiments, the textile assembly further comprises one or more of the following features, considered alone or according to any technically possible combination:

the textile assembly comprises a first textile element and a second textile element distinct from said first textile element, wherein the first textile support is part of the first textile element and the second textile support is part of the second textile element;

one of the first and second textile element is a textile element to be worn on a first part of a body, and the other one of the first and second textile element is a textile element to be worn on a second part of a body distinct from said first part;

the body is a user's body, the first and second textile element being a first and a second clothing, one of the first and second clothing being a clothing to be worn on a first part of the user's body, such as the chest, and the other one of the first and second clothing being a clothing to be worn on a second part of the user's body distinct from said first part, such as the head, a foot, a hand, a leg;

the first and second textile elements are textile elements to be worn on a same part of a body;

the body is a user's body, the first and second textile element being a first and a second clothing, the first and second clothing being clothing to be worn on a same part of the user's body, such as the chest.

Such an electrical active assembly, and the corresponding textile assembly, allow, amongst other advantages, the cross regulation between two local active relation systems. This, in turn, allows a user to wear a textile assembly with an efficient and fine physical effect active regulation on two distinct parts of his/her body or on the same part of his/her body, when he/she wears two corresponding pieces of garment.

DRAWINGS

Figure 2:
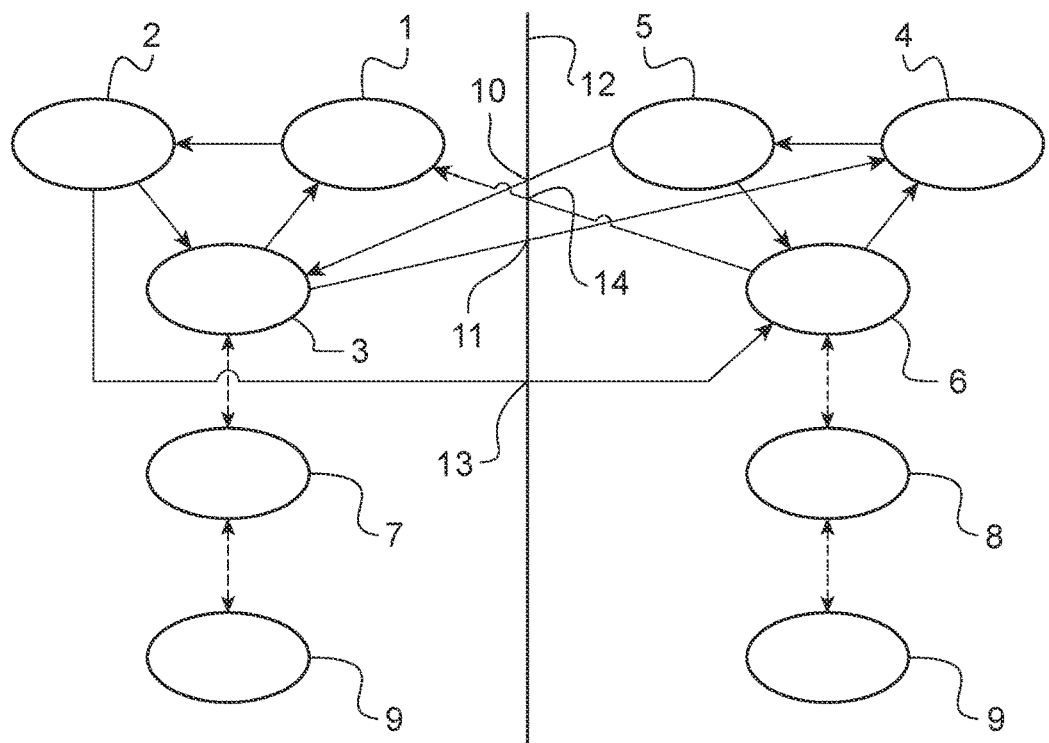

The invention and its advantages may be better understood by referring to the description which follows, given as example and for illustrative purpose only, and by referring to the accompanying drawings listed below:

FIG. 1: shows a first example of an electrical active assembly according to the invention;

FIG. 2: shows a second example of an electrical active assembly according to the invention;

DETAILED DESCRIPTION

In the two examples of FIGS. 1 and 2, the electrical active assembly of the invention aims at generating heat.

But it is to be understood that the invention extents to an electrical active assembly for generating other physical effects than heat, such as cold or relative humidity.

The electrical active assembly can be integrated in a textile assembly. Such a textile assembly comprises preferably a first textile element and a second textile element distinct from the first textile element.

The electrical active assembly comprises a first and a second textile supports, each comprising several components as will be described further in this description. The first textile support is part of the first textile element and the second textile support is part of the second textile element.

In FIGS. 1 and 2, some of the components integrated in or on the first textile support are shown on the leftmost part, and some of the components integrated in or on the second textile support are shown on the rightmost part, separated by an interface 12.

In a specific embodiment, one of the first and second textile elements is a textile element to be worn on a first part of a body, and the other one of the first and second textile elements is a textile element to be worn on a second part of a body distinct from the first part.

The body can be any sort of body, whether living or not. When dealing with a living body, it can be a human or animal body. In the specific case of a human body, or user's body, the first and second textile elements are respectively a first and a second clothing.

One of the first and second clothing is a clothing to be worn on a first part of the user's body. This can be for example the chest. The clothing can then be a t-shirt or a jacket.

The other one of the first and second clothing is a clothing to be worn on a second part of the user's body distinct from the first part. This can be for example the head, a foot, a hand, a leg. The clothing can then be a hat, cap or beanie, a sock or a shoe, a glove, trousers or a trousers leg.

In an alternative to the embodiment described above with the first and second textile elements are textile elements to be worn on two distinct part of a body, the first and second textile elements can be textile elements to be worn on a same part of a body.

Here again, the body can be any sort of body, whether living or not. When dealing with a living body, it can be a human or animal body. In the specific case of a human body, or user's body, the first and second textile elements are respectively a first and a second clothing.

The first and second textile elements are a first and a second clothing, both to be worn on a same part of the user's body, such as the chest. For example, the first clothing can be a t-shirt and the second clothing can be a jacket.

The first and second supports comprise respectively a first and a second active element 1, 4, each adapted for generating the physical effect, i.e. in the described examples, first and second active heating elements 1, 4 adapted for generating heat.

Each of these first and second active heating elements 1, 4 is adapted to be connected to a power source, and located on or in the first, respectively the second, textile supports.

The power source can be an external power source, or an internal power source integrated in the electrical active assembly. The connection with the power source can be a wired or wireless connection.

The first and second supports also comprise respectively a first and second sensors 2, 5 adapted for sensing data relative to a physical information, i.e. in the described examples a temperature sensor.

Each of these first and second sensors 2, 5 is adapted to be connected to the power source, and is located on or in the first, respectively the second, textile supports.

The first and second supports also comprise respectively a first and second controlling unit 3, 6, located on or in the first, respectively the second, textile supports.

The first controlling unit 3 is connected to the first heating element 1 and the first temperature sensor 2, and the second controlling unit 6 is connected to the second heating element 4 and the second temperature sensor 5.

The first controlling unit 3 is configured to activate/deactivate the first heating element 1 depending on data sensed by the first temperature sensor 2, and the second controlling unit 6 is configured to activate/deactivate the second heating element 4 depending on data sensed by the second temperature sensor 5.

The first controlling unit 3 is also connected to the second heating element 4 and the second temperature sensor 5, and is configured to activate/deactivate the second heating element 4 depending on data sensed by the second temperature sensor 5 and/or by the first temperature sensor 2.

Alternatively, or in combination, the second controlling unit 6 is also connected to the first heating element 1 and the first temperature sensor 2, and is configured to activate/deactivate the first heating element 1 depending on data sensed by the first temperature sensor 2 and/or by the second temperature sensor 5.

This allows therefore the control of the sensor and active element of one of the textile supports by the controlling unit of the other textile support.

The control can be indirect, as illustrated in FIG. 1, or direct as illustrated in FIG. 2, or a combination of both.

As can be seen in the example of FIG. 1, the second controlling unit 6 is connected with the first controlling unit 1 through a connection point on the interface 12. The second controlling unit 6 is configured to activate/deactivate the first heating element 1 through the first controlling unit 3, depending on data sensed by the first temperature sensor 2 and received by the second controlling unit 6 through the first controlling unit 3, and/or on data sensed by the second sensor 5 received by the second controlling unit 6.

Let us consider the application to such an electrical assembly as described above, with the leftmost part corresponding to the part of the electrical assembly integrated in or on a first textile support which is part of a t-shirt, and the rightmost part corresponding to the part of the electrical assembly integrated in or on a second textile support which is part of a glove.

Each of the these to part of the electrical assembly can work independently from each other, as two separate and independent temperature regulation systems. The glove can therefore be worn without the t-shirt, and the corresponding temperature regulation system will work to provide heat to the hand of the user.

The t-shirt can also be worn without the glove, and the corresponding temperature regulation system will work to provide heat to the chest of the user. But the two corresponding temperature regulation systems can also interact, when the t-shirt and the glove are worn together by the user.

The first control unit 3 and the second control unit 6 can communicate with each, either wirelessly (for example via a Bluetooth or infrared type communication), or with a wire connection, with a connection at the level of the interface 12, or directly on one or the other control unit 3, 6, using any type of connector, for example a snap button connector.

Alternatively, or in combination as illustrated in FIG. 1, the first controlling unit 3 is connected with the second controlling unit 6 and configured to activate/deactivate the second heating element 4 through the second controlling unit 6, depending on data sensed by the second temperature sensor 5 and received by the first controlling unit 3 through the second controlling unit 6, and/or on data sensed by the first temperature sensor 2 received by the first controlling unit 3.

In the second alternative or combined embodiment, as can be seen in the example of FIG. 2, the second heating element 4 and the second temperature sensor 5 are directly connected to the first controlling unit 3 through respective direct connection points 10, 11 on the interface 12. The first controlling unit is configured to directly activate/deactivate the second heating element 4 through the corresponding connection point 11, depending on data sensed by the second temperature sensor 5 and received by the first controlling unit 3 through the corresponding connection point 10, and/or on data sensed by the first temperature sensor 2 and received by the first or second controlling unit 3, 6.

Alternatively, or in combination as illustrated in FIG. 2, the first heating element 1 and the first temperature sensor 2 are directly connected to the second controlling unit 6 through respective direct connection points 14, 13 on the interface 12. The second controlling unit 6 is configured to directly activate/deactivate the first heating element 1 through the corresponding connection point 14, depending on data sensed by the first temperature sensor 2 and received by the second controlling unit 6 through the corresponding connection point 13, and/or on data sensed by the second temperature sensor 5 and received by the first or second controlling unit 3, 6.

Let us consider again the application to such an electrical assembly as described above, with the leftmost part corresponding to the part of the electrical assembly integrated in or on a first textile support which is part of a t-shirt, and the rightmost part corresponding to the part of the electrical assembly integrated in or on a second textile support which is part of a glove.

In that example, the glove can be physically connected to the t-shirt, using any type of connectors 10, 11, 13, 14, for example snap button connectors, at the level of the interface 12. Each of the two parts of the electrical assembly keeps its own controlling unit 3, 6, such that the control unit 3 corresponding to the t-shirt can take over the control unit 6 corresponding to the glove, and/or the control unit 6 corresponding to the glove can take over the control unit 3 corresponding to the t-shirt. This can be particularly useful in case of failure of one of the control units 3, 6, and/or in case of low energy for one of these control units 3, 6.

A user device 7, 8 can be used by the user as an input-output interface. Preferably, the same user device is used for both parts of the system, but two distinct user devices 7, 8 may also be used for each part.

The user device 7, 8 is a portable device, such as a smartphone or a tablet, that includes at least a processor, a memory and a user interface. Preferably, it is a low energy wireless device which communicates in reception and transmission using for example a Bluetooth or infra-red as wireless communication protocol.

Possibly, the power source mentioned above can be the power source of the user device 7, 8.

Each of the controlling units 3, 6 include at least a logical unit, such as a processor or microprocessor that can process electronic commands, a memory unit and a power unit. The power unit generates power and the power unit preferably comprises rechargeable batteries. The processor, memory unit and power unit are preferably arranged in a casing.

These controlling units 3, 6 can be microcontrollers, i.e. they include all components on a single chip or integrated circuit. Their logical units can execute commands stored in the corresponding memory unit such as non-transitory computer readable memory unit.

The processor is preferably in the form of an integrated circuit. The memory unit comprises a ROM and a RAM. The power unit includes one or more rechargeable batteries that are disposed in a casing and in communication with the processor. The controlling units 3, 6 also include other essential electronic components for interfacing the various components described and appropriate interfacing circuitry.

The controlling units 3, 6 further include a communication module. The communication module is a low energy wireless system such as a Bluetooth module. The communication module is in wire or wireless communication with the processor and allows the controlling units 3, 6 to communicate with the user devices 7, 8.

A local application that is executable on the user devices 7, 8 allows communication between the user devices 7, 8 and the controlling units 3, 6. The application also allows for a user to access an interface that allows a user to input for example user profile information as well as additionally modify operating modes of the controlling units 3, 6.

The user devices 7, 8 can be in connection with distant storage means 9 named cloud 9. The communication between the control units 3, 6 and the user devices 7, 8 is then necessary only at the first time the system is powered, in order to enter user parameters. These parameters are transmitted by the user devices 7, 8 to the cloud 9 for storage.

When no user devices 7, 8 are used, the control units 3, 6 are configured to allow to directly enter such user parameters and proceed to calibration, via an appropriate interface or a remote control.

Besides, all or part of the control logic to control the active elements 1, 4 depending on the information sensed by the sensors 2, 5, can be located in the user devices 7, 8, or in the cloud 9. In such a case, the good working of the system depends also on the batteries of the user devices 7, 8 and on the network coverage for communication with the cloud 9.

The controlling units 3, 6 are configured to provide an activation signal along the power lines to the heating elements 1, 4. The activation signal is preferably a pulse width modulated (PWM) power signal. The controlling units 3, 6 include a PWM module. This PWM module can be integrated into the processor or connected to the processor and the power unit. The PWM module generates a PWM signal and transmits such signal along the power lines to the appropriate heating elements. A PWM signal conserves the power from the power unit.

Besides, all or part of the control logic to control the active elements 1, 4 depending on the information sensed by the sensors 2, 5, can be located in the user devices 7, 8, and/or in the cloud 9. In this case, the corresponding parts of the user devices 7, 8 and/or of the cloud 9 are functionally parts of the controlling units 3, 6. Also, in such a case, the good working of the system depends also on the batteries of the user devices 7, 8 and on the network coverage for communication with the cloud 9.

The above description has been directed to specific embodiments of this invention which is, however, not limited to these embodiments described for purpose of example only.

The invention claimed is:

1. An electrical active assembly for generating at least one physical effect, comprising
    a first textile support;
    a first active element adapted for generating said physical effect and for being connected to a power source, and located on or in said first textile support;
    a first sensor adapted for sensing data relative to a physical information, and being connected to a power source, and located on or in said first textile support;
    and a first controlling unit connected to the first active element and the first sensor, and located on or in said first textile support;
    such as to allow the activation/deactivation by said first controlling unit of said first active element depending on data sensed by said first sensor, the electrical assembly further comprising
    a second textile support distinct from said first textile support;
    a second active element adapted for generating said physical effect and for being connected to a power source, and located on or in said second textile support;
    a second sensor adapted for sensing data relative to a physical information and being connected to a power source, and located on or in said second textile support;
    and a second controlling unit connected to the second active element and the second sensor, and located on or in said second textile support;
    such as to allow the activation/deactivation by said second controlling unit of said second active element depending on data sensed by said second sensor,
    the first controlling unit being connected to the second active element and the second sensor, such as to allow the activation/deactivation by said first controlling unit of said second active element depending on data sensed by said second sensor and/or by said first sensor, and/or the second controlling unit being connected to the first active element and the first sensor, such as to allow the activation/deactivation by said second controlling unit of said first active element depending on data sensed by said first sensor and/or by said second sensor, the second active element and the second sensor are directly connected to the first controlling unit through respective direct connection points, such as to allow the direct activation/deactivation by said first controlling unit of said second active element through the corresponding connection point, depending on data sensed by said second sensor and received by said first controlling unit through the corresponding connection point.

2. The electrical active assembly according to claim 1, wherein the first active element and the first sensor are directly connected to the second controlling unit through respective direct connection points, such as to allow the direct activation/deactivation by said second controlling unit of said first active element through the corresponding connection point, depending on data sensed by said first sensor and received by said second controlling unit through the corresponding connection point, and/or on data sensed by the second sensor and received by said first or second controlling unit.

3. The electrical active assembly according to claim 1, wherein the second controlling unit is able to connect with the first controlling unit such as to allow the activation/deactivation by the second controlling unit of the first active element through the first controlling unit, depending on data sensed by the first sensor and received by the second controlling unit through the first controlling unit, and/or on data sensed by the second sensor received by said second controlling unit.

4. The electrical active assembly according to claim 1, wherein the first controlling unit is able to connect with the second controlling unit such as to allow the activation/deactivation by the first controlling unit of the second active element through the second controlling unit, depending on data sensed by the second sensor and received by the first controlling unit through the second controlling unit, and/or on data sensed by the first sensor received by said first controlling unit.

5. A textile assembly comprising an electrical active assembly according to claim 1.

6. The textile assembly according to claim 5, comprising a first textile element and a second textile element distinct from said first textile element, wherein the first textile support is part of the first textile element and the second textile support is part of the second textile element.

7. The textile assembly according to claim 6, wherein one of the first and second textile elements is a textile element to be worn on a first part of a body, and the other one of the first and second textile elements is a textile element to be worn on a second part of a body distinct from said first part.

8. The textile assembly according to claim 7, wherein the body is a user's body, the first and second textile element being a first and a second clothing, one of the first and second clothing being a clothing to be worn on a first part of the user's body, and the other one of the first and second clothing being a clothing to be worn on a second part of the user's body distinct from said first part.

9. The textile assembly according to claim 6, wherein the first and second textile elements are textile elements to be worn on a same part of a body.

10. The textile assembly according to claim 9, wherein the body is a user's body, the first and second textile element being a first and a second clothing, the first and second clothing being clothing to be worn on a same part of the user's body.

11. The textile assembly according to claim 10, wherein the first and second clothing are clothing to be worn on the chest.

12. The textile assembly according to claim 8, wherein the first part of the user's body is the chest.

13. The textile assembly according to claim 8, wherein the second part of the user's body is the head, or a foot, or a hand, or a leg.

14. The electrical active assembly according to claim 1, wherein the physical effect is heat, cold or relative humidity.

15. The electrical active assembly according to claim 1, wherein the physical information is temperature or humidity.

* * * * *